(12) United States Patent
Yoon et al.

(10) Patent No.: US 12,128,023 B2
(45) Date of Patent: *Oct. 29, 2024

(54) PHARMACEUTICAL COMPOSITION CONTAINING β-LAPACHONE AS ACTIVE INGREDIENT FOR PREVENTION OR TREATMENT OF CHOLESTATIC LIVER DISEASE

(71) Applicant: CUROME BIOSCIENCES CO., LTD., Cheongju-si (KR)

(72) Inventors: Joo Seog Yoon, Suwon-si (KR); Kang Sik Seo, Ansan-si (KR); Jeong Su Han, Suwon-si (KR); Sung Je Moon, Daejeon (KR); Jung Hoon Lee, Suwon-si (KR); Soo Bin Yoon, Suwon-si (KR)

(73) Assignee: CUROME BIOSCIENCES CO., LTD., Cheongju-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/942,505

(22) Filed: Sep. 12, 2022

(65) Prior Publication Data
US 2023/0055593 A1    Feb. 23, 2023

Related U.S. Application Data

(63) Continuation of application No. 17/724,262, filed on Apr. 19, 2022, and a continuation of application No. PCT/KR2021/013732, filed on Oct. 6, 2021.

(30) Foreign Application Priority Data

Oct. 8, 2020 (KR) .......................... 10-2020-0130028

(51) Int. Cl.
| | | |
|---|---|---|
| *A01N 37/00* | (2006.01) | |
| *A01N 25/00* | (2006.01) | |
| *A01N 37/12* | (2006.01) | |
| *A01N 37/44* | (2006.01) | |
| *A61K 31/215* | (2006.01) | |
| *A61K 31/24* | (2006.01) | |
| *A61K 31/352* | (2006.01) | |
| *A61K 38/00* | (2006.01) | |
| *A61P 1/16* | (2006.01) | |

(52) U.S. Cl.
CPC .......... *A61K 31/352* (2013.01); *A61K 38/005* (2013.01); *A61P 1/16* (2018.01)

(58) Field of Classification Search
CPC ............................... A61K 31/352; A61P 1/16
See application file for complete search history.

(56) References Cited

U.S. PATENT DOCUMENTS

| | | |
|---|---|---|
| 8,883,856 B2 | 11/2014 | Jackson et al. |
| 9,066,922 B2 | 6/2015 | Yoo et al. |
| 2013/0245111 A1 | 9/2013 | Yoo et al. |
| 2014/0275090 A1 | 9/2014 | Gedulin et al. |
| 2020/0155500 A1 | 5/2020 | So et al. |
| 2020/0268727 A1 | 8/2020 | Miao et al. |
| 2021/0388092 A1 | 12/2021 | Abhyankar |

FOREIGN PATENT DOCUMENTS

| | | |
|---|---|---|
| CN | 101822659 A | 9/2010 |
| CN | 105056230 A | 11/2015 |
| CN | 106304835 A | 1/2017 |
| JP | 6511191 B2 | 5/2019 |
| KR | 10-2006-0092106 A | 8/2006 |
| KR | 10-1501612 B1 | 3/2015 |
| KR | 10-2016-0002773 A | 1/2016 |
| KR | 10-2016-0081588 A | 7/2016 |
| KR | 10-2017-0120622 A | 10/2017 |
| KR | 10-2019-0026687 A | 3/2019 |
| WO | 2005082358 A2 | 9/2005 |

OTHER PUBLICATIONS

Kim et al. "Melanogenesis inhibition of beta-lapachone, a natural product from Tabebuia avellanedae, with effective in vivo lightening potency," Arch Dermatol. Res. 2015, 307: 229-238 (Year: 2015).*
Byeon et al. "In vitro and in vivo anti-inflammatory effects of taheebo, a water extract from the inner bark of Tabebuia avellanedae," J. Ethonopharmacology, 2008, 119, 145-152 (Year: 2008).*
Lee et al. "Pharmacokinetic and safety evaluation of MB 12066, an NQO1 subtract," Drug Design, Development and Therapy, 2017, vol. 11, pp. 2719-2725 (Year: 2017).*
Jungst et al. "Intrahepatic cholestasis in common chronic liver diseases," European J. Clinical Investigation, 2013, vol. 43, pp. 1069-1083 (Year: 2013).*
Grattagliiano et al. "Mitochondria in Chronic Liver Disease," Current Drug Targets, 2011, vol. 12, pp. 879-893 (Year: 2011).*
Novak et al. "Mitochondrial dysfunction in inflammatory bowel disease," Frontiers in Cell and Developmental Biology, 2015, vol. 3, Article 62 (Year: 2016).*
Talwalkar et al. "Primary Sclerosing Cholangitis," Inflamm. Bowel Dis. 2005, vol. 11, No. 1, pp. 62-72 (Year: 2005).*
Bhat et al. "Transient development of anti-mitochondrial antibodies accompanies autoimmune hepatitis-sclerosing cholangitis overlap," Gut, 2009, 58, 152-153 (Year: 2009).*
Grattagliano et al., "Mitochondria in Chronic Liver Disease", Current Drug Targets, 2011, 12, 879-893.
Novak et al. "Mitochondrial dysfunction in inflammatory bowel disease", Frontiers in Cell and Developmental Biology, 2015, vol. 3, Article 62, 18 pages.

(Continued)

*Primary Examiner* — Layla Soroush
(74) *Attorney, Agent, or Firm* — ROTHWELL, FIGG, ERNST & MANBECK, P.C.

(57) ABSTRACT

The present invention relates to a pharmaceutical composition containing β-lapachone as an active ingredient for prevention or treatment of cholestatic liver disease, and can provide agents for effectively preventing and treating cholestatic liver disease.

8 Claims, 8 Drawing Sheets
Specification includes a Sequence Listing.

(56) References Cited

OTHER PUBLICATIONS

Lee, HW et al., "Pharmacokinetic and safety evaluation of MB12066, an NQO1 substrate", Drug Design, Development and Therapy, 2017:11 2719-2725.

Ambrosini, Y.M., et al., "The multi-hit hypothesis of primary biliary cirrhosis: polyinosinic-polycytidylic acid (poly I:C) and murine autoimmune cholangitis", Clin Exp Immunol, 2011, 166: 110-120.

Best, Jan, et al., "Macrophage Depletion Attenuates Extracellular Matrix Deposition and Ductular Reaction in a Mouse Model of Chronic Cholangiopathies", PLOS ONE, 2016, 11(9): e0162286, 17 pages.

Kim, Ye-Ram, et al., "The targeted delivery of the c-Src peptide complexed with schizophyllan to macrophages inhibits polymicrobial sepsis and ulcerative colitis in mice", Biomaterials, 2016, 89: 1-13.

Australian Office Action issued for Australian Application No. 2021358793 on Jun. 15, 2023, 4 pages.

Japanese Office Action issued for Japanese Application No. 2022-520836 on May 2, 2023, 9 pages.

Gijbels, E, Pieters, A, De Muynck, K, Vinken, M, Devisscher, L. Rodent models of cholestatic liver disease: A practical guide for translational research. Liver Int. 2021; 41: 656-682. https://doi.org/10.1111/liv.14800.

Sato K, Glaser S, Kennedy L, et al. Preclinical insights into cholangiopathies: disease modeling and emerging therapeutic targets. Expert Opin Ther Targets. 2019;23(6):461-472. https://doi:10.1080/14728222.2019.1608950.

Mariotti V, Strazzabosco M, Fabris L, et al. Animal models of biliary injury and altered bile acid metabolism. Biochim Biophys Acta Mol Basis Dis. 2018; 1864:1254-1261.

Gayathri AK, Padmanaban G. Biochemical effects of 3,5-diethoxycarbonyl-1,4-dihydrocollidine in mouse liver. Biochem Pharmacol. 1974;23:2713-2725.

Fickert P, Pollheimer MJ, Christoph HÖ, et al. Chapter 15: Animal models of cholestasis. Animal models for the study of human disease. 2013:331-349.

Fickert P, Stöger U, Fuchsbichler A, et al. A new xenobioticinduced mouse model of sclerosing cholangitis and biliary fibrosis. Am J Pathol. 2007;171:525-536.

Okada C, Akbar SM, Horiike N, et al. Early development of primary biliary cirrhosis in female C57BL/6 mice because of poly I:C administration. Liver Int. 2005;25:595-603. [PubMed: 15910497].

Jiang T, Han Z, Chen S, et al. Resistance to activation-induced cell death and elevated FLIPL expression of CD4+ T cells in a polyI:C-induced primary biliary cirrhosis mouse model. Clin Exp Med. 2009;9:269-76. [PubMed: 19418018].

Fickert P, Pollheimer MJ, Beuers U, Lackner C, Hirschfield G, Housset C, Keitel V, Schramm C, Marschall HU, Karlsen TH, Melum E, Kaser A, Eksteen B, Strazzabosco M, Manns M, Trauner M, P.S.C.S.G. International Characterization of animal models for primary sclerosing cholangitis (PSC) J Hepatol. 2014;60:1290-1303.

Pollheimer MJ, Fickert P. Animal models in primary biliary cirrhosis and primary sclerosing cholangitis. Clin Rev Allergy Immunol. 2015;48:207-217.

Vierling JM. Animal models for primary sclerosing cholangitis. Best Pract Res Clin Gastroenterol. 2001;15:591-610.

Fickert P, Trauner M, Fuchsbichler A, Stumptner C, Zatloukal K, Denk H. Bile acid-induced Mallory body formation in drug-primed mouse liver. Am J Pathol. 2002;161:2019-2026.

Hanada S, Strnad P, Brunt EM, Omary MB. The genetic background modulates susceptibility to mouse liver Mallory-Denk body formation and liver injury. Hepatology. 2008;48:943-952.

Fickert P, Thueringer A, Moustafa T, Silbert D, Gumhold J, Tsybrovskyy O, Lebofsky M, Jaeschke H, Denk H, Trauner M. The role of osteopontin and tumor necrosis factor alpha receptor-1 in xenobiotic-induced cholangitis and biliary fibrosis in mice. Lab Investig. 2010;90:844-852.

Calvisi DF, Thorgeirsson SS. Molecular mechanisms of hepatocarcinogenesis in transgenic mouse models of liver cancer. Toxicol Pathol. 2005;33:181-184.

French SW, Lee J, Zhong J, Morgan TR, Buslon V, Lungo W, French BA. Alcoholic liver disease—hepatocellular carcinoma transformation. J Gastrointest Oncol. 2012;3:174-181.

Liedtke C, Luedde T, Sauerbruch T, Scholten D, Streetz K, Tacke F, Tolba R, Trautwein C, Trebicka J, Weiskirchen R. Experimental liver fibrosis research: update on animal models, legal issues and translational aspects. Fibrogenesis Tissue Repair. 2013;6:19.

Lindor KD. Ursodiol for primary sclerosing cholangitis. Mayo primary sclerosing cholangitis-ursodeoxycholic acid study group. N Engl J Med. 1997;336(10):691-5. https://doi.org/10.1056/NEJM199703063361003. Medline: 9041099.

Beuers U, Spengler U, Kruis W, et al. Ursodeoxycholic acid for treatment of primary sclerosing cholangitis: a placebo- controlled trial. Hepatology. 1992;16(3):707-14. https://doi.org/10.1002/hep.1840160315. Medline: 1505913.

Chazouilleres O, Poupon R, Capron JP, et al. Ursodeoxycholic acid for primary sclerosing cholangitis. J Hepatol. 1990;11(1):120-3. https://doi.org/10.1016/0168-8278(90)90281-U. Medline: 1975818.

Stiehl A, Walker S, Stiehl L, Rudolph G, Hofmann WJ, Theilmann L. Effect of ursodeoxycholic acid on liver and bile duct disease in primary sclerosing cholangitis. A 3-year pilot study with a placebo-controlled study period. J Hepatol. 1994;20(1):57-64. https://doi.org/10.1016/S0168-8278(05)80467-2. Medline: 8201224.

Van Hoogstraten HJ, Wolfhagen FH, van de Meeberg PC, et al. Ursodeoxycholic acid therapy for primary sclerosing cholangitis: results of a 2-year randomized controlled trial to evaluate single versus multiple daily doses. J Hepatol. 1998;29(3): 417-23. https://doi.org/10.1016/S0168-8278(98)80059-7. Medline: 9764988.

Cullen SN, Rust C, Fleming K, Edwards C, Beuers U, Chapman RW. High dose ursodeoxycholic acid for the treatment of primary sclerosing cholangitis is safe and effective. J Hepatol. 2008;48(5):792-800. https://doi.org/10.1016/j.jhep.2007.12.023. Medline: 18314215.

Mitchell SA, Bansi DS, Hunt N, Von Bergmann K, Fleming KA, Chapman Rw. A preliminary trial of high-dose ursodeoxycholic acid in primary sclerosing cholangitis. Gastroenterology. 2001; 121(4):900-7. https://doi.org/10.1053/gast.2001.27965. Medline: 11606503.

Olsson R, Boberg KM, de Muckadell OS, et al. High-dose ursodeoxycholic acid in primary sclerosing cholangitis: a 5-year multicenter, randomized, controlled study. Gastroenterology. 2005;129(5):1464-72. https://doi.org/10.1053/j.gastro.2005.08.017. Medline: 16285948.

Lindor KD, Kowdley KV, Luketic VA, et al. High-dose ursodeoxycholic acid for the treatment of primary sclerosing cholangitis. Hepatology. 2009;50(3):808-14. https://doi.org/10.1002/hep.23082. Medline: 19585548.

Harnois DM, Angulo P, Jorgensen RA, Larusso NF, Lindor KD. High-dose ursdeoxycholic acid as a therapy for patients with primary sclerosing cholangitis. Am J Gastroenterol. 2001;96(5):1558-62. https://doi.org/10.1111/j.1572-0241.2001.03777.x. Medline: 11374699.

Lo SK, Hermann R, Chapman RW, et al. Ursodeoxycholic acid in primary sclerosing cholangitis: a double-blind placebo controlled trial. Hepatology. 1992;16(4):92A.

Triantos CK, Koukias NM, Nikolopoulou VN, Burroughs AK. Meta-analysis: ursodeoxycholic acid for primary sclerosing cholangitis. Aliment Pharmacol Ther. 2011;34(8):901-10. https://doi.org/10.1111/j.1365-2036.2011.04822.x. Medline: 21883323.

European Association for the Study of the Liver. EASL Clinical Practice Guidelines: The diagnosis and management of patients with primary biliary cholangitis. J Hepatol 2017;67:145-172.

Lindor KD, Bowlus CL, Boyer J, Levy C, Mayo M. Primary Biliary Cholangitis: 2018 Practice Guidance from the American Association for the Study of Liver Diseases. Hepatology 2019;69:394-419.

Corpechot C, Carrat F, Bahr A, Chretien Y, Poupon RE, Poupon R. The effect of ursodeoxycholic acid therapy on the natural course of primary biliary cirrhosis. Gastroenterology 2005;128:297-303.

Ter Borg PC, Schalm SW, Hansen BE, van Buuren HR, Dutch PBCSG. Prognosis of ursodeoxycholic Acid-treated patients with primary biliary cirrhosis. Results of a 10-yr cohort study involving 297 patients. Am J Gastroenterol 2006;101:2044-2050.

(56) References Cited

OTHER PUBLICATIONS

Pares A, Caballeria L, Rodes J. Excellent long-term survival in patients with primary biliary cirrhosis and biochemical response to ursodeoxycholic Acid. Gastroenterology 2006; 130:715-720.
Poupon RE, Poupon R, Balkau B. Ursodiol for the long-term treatment of primary biliary cirrhosis. The UDCA-PBC Study Group. N Engl J Med 1994;330:1342-1347.
Heathcote EJ, Cauch-Dudek K, Walker V, Bailey RJ, Blendis LM, Ghent CN, et al. The Canadian Multicenter Double- blind Randomized Controlled Trial of ursodeoxycholic acid in primary biliary cirrhosis. Hepatology 1994;19:1149-1156.
Lindor KD, Dickson ER, Baldus WP, Jorgensen RA, Ludwig J, Murtaugh PA, et al. Ursodeoxycholic acid in the treatment of primary biliary cirrhosis. Gastroenterology 1994;106:1284-1290.
Papatheodoridis GV, Hadziyannis ES, Deutsch M, Hadziyannis SJ. Ursodeoxycholic acid for primary biliary cirrhosis: final results of a 12-year, prospective, randomized, controlled trial. Am J Gastroenterol 2002;97:2063-2070.
Combes B, Carithers RL, Jr., Maddrey WC, Lin D, McDonald MF, Wheeler DE, et al. A randomized, double-blind, placebo-controlled trial of ursodeoxycholic acid in primary biliary cirrhosis. Hepatology 1995;22:759-766.
Kilmurry MR, Heathcote EJ, Cauch-Dudek K, O'Rourke K, Bailey RJ, Blendis LM, et al. Is the Mayo model for predicting survival useful after the introduction of ursodeoxycholic acid treatment for primary biliary cirrhosis? Hepatology 1996;23:1148-1153.
Pares A, Caballeria L, Rodes J, Bruguera M, Rodrigo L, Garcia-Plaza A, et al. Long-term effects of ursodeoxycholic acid in primary biliary cirrhosis: results of a double-blind controlled multicentric trial. UDCA—Cooperative Group from the Spanish Association for the Study of the Liver. J Hepatol 2000;32:561-566.
Goulis J, Leandro G, Burroughs AK. Randomised controlled trials of ursodeoxycholic-acid therapy for primary biliary cirrhosis: a meta-analysis. Lancet 1999;354:1053-1060.
Gong Y, Huang Z, Christensen E, Gluud C. Ursodeoxycholic acid for patients with primary biliary cirrhosis: an updated systematic review and meta-analysis of randomized clinical trials using Bayesian approach as sensitivity analyses. Am J Gastroenterol 2007;102:1799-1807.
Rudic JS, Poropat G, Krstic MN, Bjelakovic G, Gluud C. Ursodeoxycholic acid for primary biliary cirrhosis. Cochrane Database Syst Rev 2012;12:CD000551.
Saffioti F, Gurusamy KS, Eusebi LH, Tsochatzis E, Davidson BR, Thorburn D. Pharmacological interventions for primary biliary cholangitis: an attempted network meta-analysis. Cochrane Database Syst Rev 2017;3:CD011648.
Neuberger J. URSO—panacea or placebo? Hepatology 2000;31:1027-1028.
Combes B, Luketic VA, Peters MG, Zetterman RK, Garcia-Tsao G, Munoz SJ, et al. Prolonged follow-up of patients in the U.S. multicenter trial of ursodeoxycholic acid for primary biliary cirrhosis. Am J Gastroenterol 2004;99:264-268.
Tsochatzis EA, Feudjo M, Rigamonti C, Vlachogiannakos J, Carpenter JR, Burroughs AK. Ursodeoxycholic acid improves bilirubin but not albumin in primary biliary cirrhosis: further evidence for nonefficacy. Biomed Res Int 2013;2013:139763.
Tsochatzis EA, Gurusamy KS, Gluud C, Burroughs AK. Ursodeoxycholic acid and primary biliary cirrhosis: EASL and AASLD guidelines. J Hepatol 2009;51:1084-1085; author reply 1085-1086.
Clerbaux, L.-A., Hul, N. V., Gouw, A. S. H., Manco, R., Español-Suñer, R., & Leclercq, I. A. (2018). Relevance of the CDE and DDC Mouse Models to Study Ductular Reaction in Chronic Human Liver Diseases. InTech. doi: 10.5772/intechopen.69533.
Shin, S. et al. "β-Lapachone alleviates alcoholic fatty liver disease in rats", Cellular signalling, 2014, vol. 26, pp. 295-305.

Zhao, Q. et al. "PPARα activation protects against cholestatic liver injury", Scientific reports, 2017, vol. 7, No. 9967, pp. 1-13.
Wang, P. et al. "Promising therapy candidates for liver fibrosis", Frontiers in physiology, 2016; vol. 7, No. 47, pp. 1-9.
Lazaridis, KN. et al. "Primary Sclerosing Cholangitis", New England Journal of Medicine, 2016; 375(12): 1161-1170.
Kummen, M. et al. "Liver abnormalities in bowel diseases", Best Practice & Research. Clinical Gastroenterology, 2013; 27(4): 531-542.
Tabibian, JH. et al. "Ursodeoxycholic acid in primary sclerosing cholangitis: If withdrawal is bad, then administration is good (right?)", Hepatology, 2014; 60(3): 785-788.
Lindor, KD. et al. "ACG Clinical Guideline: Primary Sclerosing Cholangitis", American Journal of Gastroenterology, 2015; 110(5): 646-659.
Cosnes, J. et al. "Long-term evolution of disease behavior of Crohn's disease", Inflammatory Bowel Diseases, 2002; 8(4): 244-250.
Choi, CH. et al. "Second Korean guidelines for the management of ulcerative colitis", Intestinal Research, 2017; 15(1): 7-37.
Kaplan, GG. et al. "Understanding and preventing the global increase of inflammatory bowel disease", Gastroenterology, 2017; 152: 313-321.
Anderson, RM. et al. "Nicotinamide and PNC1 govern lifespan extension by calorie restriction in *Saccharomyces cerevisiae*", Nature, 2003; 423(6936): 181-185.
Luis Rajman, et al. "Therapeutic potential of NAD-boosting molecules: the in vivo evidence", Cell Metabolism, 2018, 27(3): 529-547.
Hwang, JH. et al. "Pharmacological stimulation of NADH oxidation ameliorates obesity and related phenotypes in mice", Diabetes, 2009, 58: 965-974.
James H. Tabibian, et al. "Cholangiocyte Senescence by Way of N-Ras Activation Is a Characteristic of Primary Sclerosing Cholangitis", Hepatology, 2014; 59: 2263-2275.
Sara Al-Ghadban, et al. "Cross-talk between intestinal epithelial cells and immune cells in inflammatory bowel disease", Scientific Reports, 2016; 6:29783, pp. 1-13.
Elisa Pose, et al. "3,5-Diethoxycarbonyl-1,4-Dihydrocollidine Diet: A Rodent Model in Cholestasis Research", Methods in Molecular Biology, 2019; 1981: 249-257.
Richard S. Hotchkiss, et al. "TAT-BH4 and TAT-Bcl-XL Peptides Protect against Sepsis-Induced Lymphocyte Apotosis In Vivo", Journal of Immunology, 2006; 176(9): 5471-5477.
Steven M. Opal, et al. "Effect of Eritoran, an Antagonist of MD2-TLR4, on Mortality in Patients with Severe Sepsis: The Access Randomized Trial", JAMA, 2013; 309(11): 1154-1162.
Chul-Su Yang, et al. "The autophagy regulator Rubicon is a feedback inhibitor of CARD9-mediated host innate Immunity", Cell Host & Microbe, 2012; 11(3): 277-289.
Vojo Deretic, et al. "Autophagy, Immunity, and Microbial Adaptations", Cell Host & Microbe, 2009; 5: 527-549.
Takaaki Higashi, et al. "Hepatic stellate cell as key target in liver fibrosis", Advanced Drug Delivery Reviews, 2017; 121: 27-42.
Dai et al., "Inhibition of JNK signalling mediates PPARα-dependent protection against intrahepatic cholestasis by fenofibrate," British Journal of Pharmacology, Wiley-Blackwell, UK, 174(18), Aug. 10, 2017, pp. 3000-3017.
Mokarizadeh et al., "An evaluation on potential anti-inflammatory effects of β-lapachone," International Immunopharmacology, Elsevier, Amsterdam, NL, vol. 87, Jul. 21, 2020, pp. 1-8.
Oh et al., "Increased Cellular NAD+ Level through NQO1 Enzymatic Action Has Protective Effects on Bleomycin-Induced Lung Fibrosis in Mice," Tuberc Respir Dis., 79(4), Jan. 1, 2016, pp. 257-266.
Extended Euroepan Search Report issued for European Patent Application No. 21870563.0 on Jan. 16, 2024, 10 pages.

* cited by examiner

PHARMACEUTICAL COMPOSITION CONTAINING B-LAPACHONE AS ACTIVE INGREDIENT FOR PREVENTION OR TREATMENT OF CHOLESTATIC LIVER DISEASE

CROSS-REFERENCE TO RELATED APPLICATION(S)

This application is a Continuation of U.S. application Ser. No. 17/724,262 filed on Apr. 19, 2022, which is a Continuation of PCT/KR2021/013732 filed on Oct. 6, 2021, designating the United States, which claims the benefits of filing date of Korean Patent Application No. 10-2020-0130028 filed on Oct. 8, 2020, the entire contents of which are incorporated herein by reference.

The application includes an electronically submitted Sequence Listing in .xml format. The .xml format contains a sequence listing entitled "3738-180US3.xml" created on Sep. 27, 2022 and is 21,301 bytes in size. The sequence listing contained in this .xml file is part of the specification and is incorporated by reference herein in its entirety.

TECHNICAL FIELD

Technical Field

The present disclosure relates to a pharmaceutical composition containing β-lapachone as an active ingredient for prevention or treatment of cholestatic liver disease.

Background Art

Cholestatic liver disease is a liver disease caused by a disorder of bile formation or flow. Cholestasis refers to all of biochemical, physiological, and clinical changes due to the circulatory disorder of bile produced in the liver and circulating through the biliary tract and intestine.

Primary biliary cirrhosis (PBC), a typical symptom of cholestatic liver disease, is an autoimmune disease of the liver characterized by the slow progressive destruction of the small bile ducts of the liver, with the intralobular ducts affected early in the disease. When these ducts are damaged, bile builds up in the liver (cholestasis) and over time damages the tissue, and this can lead to scarring, fibrosis, and cirrhosis.

Bile plays a key role in helping the absorption of fat and vitamins by delivering bile acids (salts) to the intestine, in addition to the function of excreting wastes in the body. The bile is produced in hepatocytes, secreted into the biliary tracts via bile canaliculi, and then undergoes enterohepatic circulation via the duodenum. When a disorder is caused in such a bile secretion process, cholestasis occurs and bile components, such as bile acids and bilirubin, are stored in hepatocytes and blood, or the bile to be delivered to the intestine is decreased to result in jaundice, pruritus, gray stool, steatorrhea, and vitamin malabsorption and, in severe cases, to develop into liver failure, which may result in a liver transplant.

Primary sclerosing cholangitis (PSC) is characterized by inflammation and fibrosis of the bile ducts that usually allow bile to drain from the gallbladder and is a long-term progressive disease of the liver and gallbladder. PSC may be asymptomatic in the early stage and may show signs and symptoms of liver disease, such as yellow discoloration of the skin and eyes, itching, and abdominal pain.

The bile duct damage by PSC narrows the ducts of the biliary tree and obstructs the flow of bile into the intestine, eventually resulting in cirrhosis and liver failure. PSC increases the risk of various cancers, including liver cancer, gallbladder cancer, colorectal cancer, and cholangiocarcinoma. Although the root cause of PSC is unknown, genetic susceptibility, immune system dysfunction, and abnormal composition of the gut flora may make a significant contribution. This is most highly relevant to IBD patients in that a high percentage of PSC patients suffer from inflammatory bowel disease (IBD), most commonly ulcerative colitis. About 3-7.5% of IBD patients suffer from PSC, and 80% of PSC patients suffer from some types of IBD.

There is no known effective therapy for PSC so far, which is generally known to occur mainly in young people in their 30 s or 40 s, and the most infallible cure is a liver transplant, but there is a risk of recurrence even after transplantation. There is not yet an approved medicine targeting PSC by the U.S. Food and Drug Administration (FDA). Some experts recommend ursodeoxycholic acid (hereafter referred to as UDCA), which lowers elevated liver enzyme levels in PSC patients and has been validated to be effective in other cholestatic liver diseases. However, the effects of ameliorating PSC symptoms and improving patient survivals by UDCA have not yet been clearly revealed. The guidelines from the American Association for the Study of Liver Diseases and the American College of Gastroenterology do not recommend the use of UDCA for the treatment of PSC, but the European Association for the Study of the Liver recommends the use of an intermediate dose (13-15 mg/kg) of UDCA. Therefore, only liver transplantation is a proven treatment for PSC so far. However, there is an urgent need to develop an effective treatment for PSC since all patients cannot receive liver transplantation.

IBD, which is suffered from by 80% of PSC patients, is one of the chronic recurrent inflammatory diseases of the gastrointestinal tract of unknown cause, represented by ulcerative colitis (UC) and Crohn's disease (CD). Exacerbated and ameliorated symptoms are repeated during the course of the disease, and later result in serious complications, such as stenosis or perforation. It was reported in the past that the incidence is relatively low in Asian countries compared with Western countries, but the prevalence of IBD is increasing worldwide, and the rate of increase is higher in Asian countries than in Western countries. Considering that IBD, unlike other chronic diseases, has a high risk of developing in the younger age group, this needs to be managed very carefully in social and economic aspects.

Meanwhile, β-lapachone (hereinafter, BL), which is a quinone-based compound, has been obtained from the *Lapacho* tree and used for the medical purposes for a long time. BL was identified both in-vitro and in-vivo to receive two electrons from NADH through the intracellular NQO1 enzyme (NAD(P)H:quinone oxidoreductase) to promote the conversion to $NAD^+$, and especially was validated in studies of NQO1-defective (knock-out) cells. However, no studies have been conducted where BL is applied to cholestatic liver disease as a $NAD^+$-promoter.

DISCLOSURE OF INVENTION

Technical Problem

An aspect of the present disclosure is to provide a pharmaceutical composition containing β-lapachone as an active ingredient for prevention or treatment of cholestatic liver disease.

Another aspect of the present disclosure is to provide a pharmaceutical composition containing β-lapachone as an active ingredient for prevention or treatment of cholestatic liver disease and inflammatory bowel disease.

Solution to Problem

The present disclosure provides a pharmaceutical composition for prevention or treatment of cholestatic liver disease, the pharmaceutical composition containing β-lapachone or a pharmaceutically acceptable salt thereof as an active ingredient.

Furthermore, the present disclosure provides a pharmaceutical composition for prevention or treatment of cholestatic liver disease, the pharmaceutical composition containing a compound represented by Chemical Formula 1 below or a pharmaceutically acceptable salt thereof as an active ingredient:

[Chemical Formula 1]

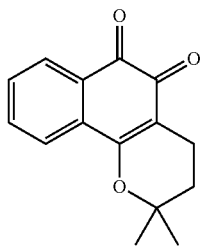

The cholestatic liver disease may be at least one selected from the group consisting of primary biliary cirrhosis (PBC), primary sclerosing cholangitis (PSC), progressive familial intrahepatic cholestasis (PFIC), benign recurrent intrahepatic cholestasis, intrahepatic cholestasis of pregnancy (ICP), cholestasis caused by viral hepatitis, cholestasis caused by alcoholic hepatitis, drug-induced cholestasis, cholestasis during parenteral nutrition, cholestasis due to malignant tumor, post-liver transplantation cholestasis, infectious cholestasis, and Alagille syndrome (AS) and, more preferably, provides a pharmaceutical composition for prevention or treatment of primary sclerosing cholangitis (PSC), primary biliary cirrhosis (PBC), benign recurrent intrahepatic cholestasis, or Alagille syndrome.

The β-lapachone (BL) may be used in the form of a pharmaceutically acceptable salt, wherein the salt may also be prepared as an acid addition salt formed by a pharmaceutically acceptable free acid, or as a pharmaceutically acceptable metal salt using a base, but is not limited thereto. Examples of the free acid may include inorganic acids and organic acids. Hydrochloric acid, hydrobromic acid, sulfuric acid, phosphoric acid, or the like may be used as an inorganic acid, and citric acid, acetic acid, lactic acid, maleic acid, gluconic acid, methanesulfonic acid, succinic acid, 4-toluenesulfonic acid, glutamic acid, aspartic acid, or the like may be used as an organic acid.

The pharmaceutical composition for prevention or treatment of cholestatic liver disease of the present disclosure is characterized by especially inhibiting fibrosis and inflammatory cytokines of cholangiocytes.

In addition, the composition is characterized by improving the level of at least one selected from the group consisting of AST, ALT, ALP, and bilirubin in the blood.

The pharmaceutical composition for prevention or treatment of cholestatic liver disease of the present disclosure is characterized by inhibiting fibrosis and inflammation, wherein the inhibiting of fibrosis is characterized by inhibiting at least one selected from fibrosis factors consisting of collagen type I alpha 1 (Col1α1), collagen type IV alpha 1 (Col4α1), alpha-smooth muscle actin (α-SMA), fibronectin, transforming growth factor beta 1 (TGF-β1), collagen type I alpha 2 (Col1α2), and transforming growth factor beta 2 (TGF-β2).

The inhibiting of inflammation is characterized by inhibiting at least one selected from inflammatory cytokine factors consisting of interleukin-1beta (IL-1β), interleukin-6 (IL-6), interleukin-18 (IL-18), interferon-γ (INF-γ), tumor necrosis factor-α (TNF-α), tumor necrosis factor-β (TNF-β), monocyte chemoattractant protein-1 (MCP-1).

In addition, the pharmaceutical composition for prevention or treatment of cholestatic liver disease is characterized by having a superior effect in the cholestatic liver disease accompanied by inflammatory bowel disease (IBD), wherein the inflammatory bowel disease (IBD) is Crohn's disease (CD) or ulcerative colitis (UC).

The composition of the present disclosure is characterized in that a composition further containing ursodeoxycholic acid (UDCA) or obeticholic acid (OCA) exhibits a superior effect in cholestatic liver disease compared with the administration thereof alone.

The β-lapachone may be added at an amount of preferably 0.001-50 wt %, more preferably 0.001-40 wt %, and most preferably 0.001-30 wt %, relative to a total weight of the entire pharmaceutical composition.

The pharmaceutical composition may be formulated in an oral dosage form, such as a powder, granules, a tablet, a capsule, a suspension, an emulsion, a syrup, a liquid, or an aerosol, and in the form of an external preparation, a suppository, and a sterile injectable solution, according to a conventional method for each form. Examples of a carrier, a vehicle, and a diluent that may be contained in the pharmaceutical composition may include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and a mineral oil. Specifically, the pharmaceutical composition, when formulated as a preparation, may be formulated using a diluent or an excipient, such as a filler, an extender, a binder, a wetting agent, a disintegrant, a surfactant, a sweetening agent, or an acidifier, which are commonly used. Exemplary solid preparations for oral administration include a tablet, a pill, a powder, granules, a capsule, and the like. These solid preparations may be prepared by mixing β-lapachone of the present disclosure with at least one excipient, for example, starch, calcium carbonate, sucrose or lactose, gelatin, or the like. In addition to simple excipients, lubricants, such as magnesium stearate and talc, may be used. Exemplary liquid preparations for oral administration correspond to a suspension, an oral liquid preparation, an emulsion, a syrup, and the like, and these liquid preparations may contain simple diluents that are frequently used, such as water and liquid paraffin, as well as several types of excipients, such as a wetting agent, a sweetening agent, a flavoring agent, a preservative, and an acidifier. Exemplary preparations for parenteral administration include a sterile aqueous solution, a non-aqueous solvent, a suspension, an emulsion, a freeze-dried preparation, and a suppository. Examples of the non-aqueous solvent and the suspension may include propylene glycol, polyethylene glycol, a vegetable oil such as olive oil, an injectable ester such as ethyl oleate, and the like. Examples of a substrate for the suppository may include Witepsol, Macrogol, Tween-61, cacao butter, laurin butter, glycerogelatin, and the like.

The dose of the pharmaceutical composition of the present disclosure may vary depending on the age, sex, and body weight of a subject to be treated, the particular disease or pathological condition to be treated, the severity of a disease or pathological condition, the route of administration, and the judgment of a prescriber. The determination of the dose based on these factors is within the level of a person skilled in the art, and the general dose is in the range of approximately 0.01 mg/kg/day to 500 mg/kg/day. A preferable dose is 0.1 mg/kg/day to 200 mg/kg/day, and a more preferable dose is 1 mg/kg/day to 200 mg/kg/day. The administration may be performed once or several times in divided doses per day. The dose is not intended to limit the scope of the present disclosure in any aspect.

The pharmaceutical composition of the present disclosure may be administered to mammals, such as mice, livestock, and humans, through various routes. All modes of administration may be contemplated, for example, administration may be performed by oral, rectal, intravenous, intramuscular, subcutaneous, intrauterine dural, or intracerebrovascular injection, and via application to the skin. The pharmaceutical composition containing β-lapachone of the present disclosure has little toxicity and side effects, and thus is a medicine that can be safely used even for long-term administration for preventive purposes.

The present disclosure relates to a health functional food for prevention or amelioration of cholestatic liver disease, the heath functional food containing β-lapachone as an active ingredient.

The present disclosure relates to a health functional food for prevention or symptom amelioration of cholestatic liver disease accompanied by inflammatory bowel disease, the heath functional food containing β-lapachone as an active ingredient. The inflammatory bowel disease may be Crohn's disease or ulcerative colitis.

The health functional food containing β-lapachone as an active ingredient for prevention or amelioration of cholestatic liver disease may further contain ursodeoxycholic acid (UDCA) or obeticholic acid (OCA).

In the health functional food, a composition containing β-lapachone (BL) may be added at an amount of preferably 0.001-50 wt %, more preferably 0.001-30 wt %, and most preferably 0.001-10 wt %, relative to a total weight of the entire food.

The health functional food refers to a food that is manufactured and processed in the form of a tablet, a capsule, a powder, pills, or a liquid by using functional raw materials or ingredients useful for the human body. The term functional means controlling nutrients for the structure or functions of the human body or obtaining beneficial effects to health care purposes, such as physiological actions. The health functional food of the present disclosure may be manufactured by a method that is commonly used in the art, and in the manufacturing of the food, the food may be manufactured by adding raw materials and ingredients that are commonly added in the art.

Advantageous Effects of Invention

The present disclosure is directed to a pharmaceutical composition for prevention or treatment of cholestatic liver disease, the pharmaceutical composition containing β-lapachone as an active ingredient, and the pharmaceutical composition can be used as an effective agent for prevention and treatment of cholestatic liver disease.

Furthermore, the pharmaceutical composition containing β-lapachone as an active ingredient for prevention or treatment of cholestatic liver disease was identified to have effects of inhibiting fibrosis and inflammation, and thus can be used as agents for effectively preventing and treating cholestatic liver disease.

BEST MODE FOR CARRYING OUT THE INVENTION

Figure 1:
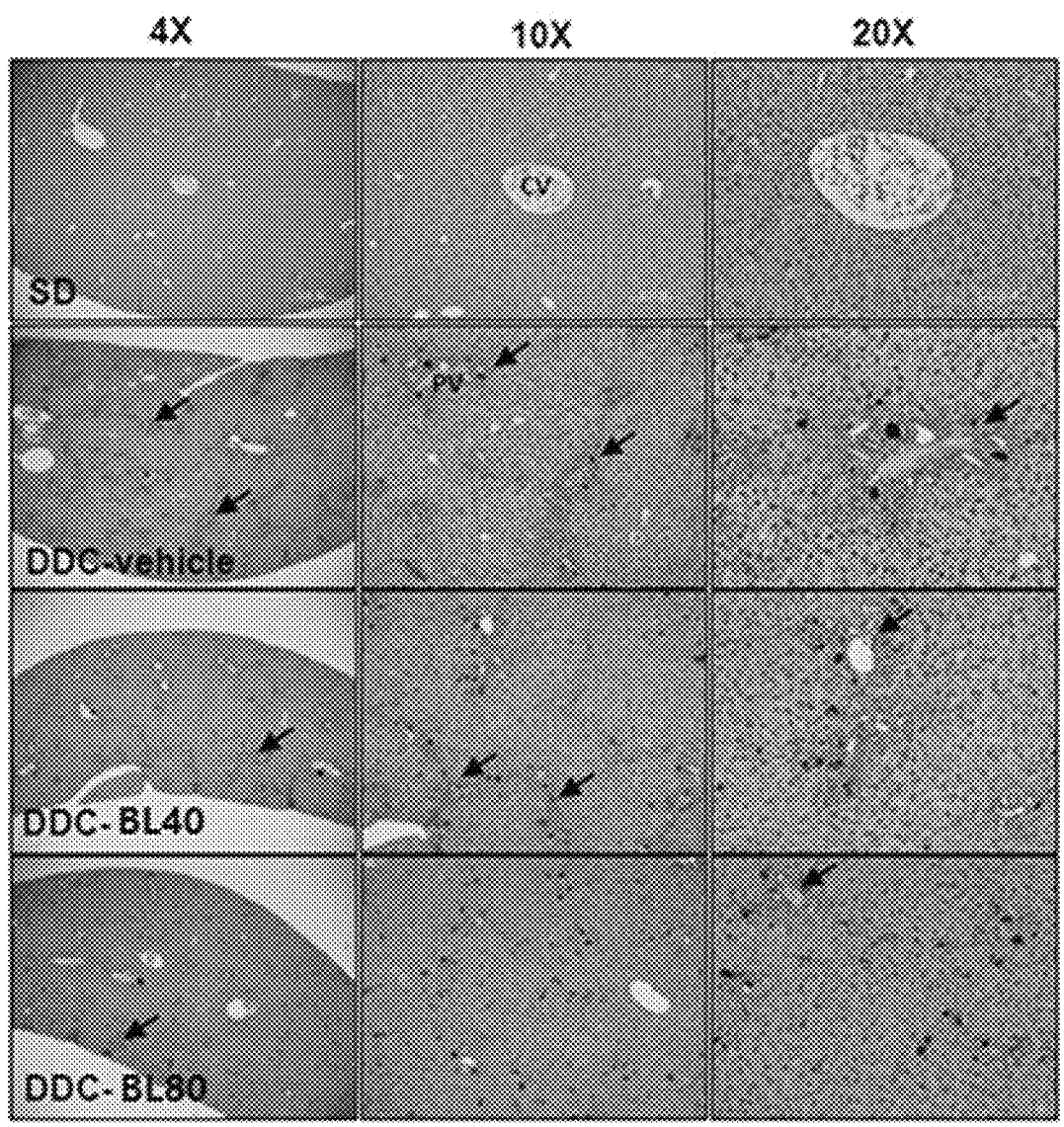
FIG. 1 shows images of the tissue surrounding the portal vein (PV) after the application or non-application of β-lapachone (BL) in DDC-induced cholestatic liver disease animal models.

Hereinafter, unless otherwise specified, β-lapachone is used as a concept encompassing β-lapachone itself and pharmaceutically acceptable salts thereof.

The causes of cholestasis are very diverse, such as various drug side effects, infections, tumors, bile duct tumors, cysts, bile duct stone, stenosis, and physical pressure on the bile ducts, and examples of cholestatic liver disease according to causes include primary biliary cirrhosis (PBC), primary sclerosing cholangitis (PSC), progressive familial intrahepatic cholestasis (PFIC), benign recurrent intrahepatic cholestasis, intrahepatic cholestasis of pregnancy (ICP), cholestasis caused by viral hepatitis, cholestasis caused by alcoholic hepatitis, drug-induced cholestasis, cholestasis during parenteral nutrition, cholestasis due to malignant tumor, post-liver transplantation cholestasis, infectious cholestasis, and Alagille syndrome (AS).

Hereinafter, preferable exemplary embodiments of the present disclosure will be described in detail. However, the present disclosure is not limited to the exemplary embodiments described herein and can be embodied in many different forms. Rather, these exemplary embodiments are provided so that the present disclosure will be thorough and complete and will fully convey the scope of the disclosure to those skilled in the art.

Example 1: Construction of Cholestatic Liver Disease Mouse Animal Models 3,5-Diethoxycarbonyl-1,4-dihydrocollidine (DDC) inhibits the activity of ferrochelatase, which inserts Fe into protoporphyrin IX to generate heme, to induce the accumulation of protoporphyrin in the liver, and the accumulation and crystallization in the bile ducts due to the characteristics of hydrophobic protoporphyrin that can be excreted out of the liver only through the bile causes inflammation and fibrosis inside and outside the bile ducts. Since cholestasis, inflammation, and fibrosis in the liver tissue are induced by the above mechanism, DDC diet-induced animal models are one of the most used rodent cholestatic liver disease animal models.

DDC-induced cholestatic liver disease mouse animal models were prepared according to the method of Elisa Pose et al. by using 8-week-old C57BL/6 male mice (Samtako, Korea). Briefly, cholestatic liver disease was induced by feeding a standard rodent diet supplemented with 0.1% (w/w) DDC for 7 or 14 days. The 12-hour light and dark cycle was maintained and animals were allowed to free access to water. The standard rodent diet included medium wheat, wheat, corn, and corn gluten flour, and soybean oil (14% protein). All animal related procedures were reviewed and approved by the Institutional Animal Care and Use Committee of Korea Research Institute of Bioscience and Biotechnology (KRIBB), KRIBB-AEC-20165).

Example 2: Preventive Effect of β-Lapachone on Lesions in Cholestatic Liver Disease Mouse Animal Models 2.1. Histology Analysis of Cholestatic Liver Disease Mouse Animal Models The long-term supply of DDC results in porphyrin plugs in the ducts to damage the biliary epithelium, thereby inducing duct obstruction. A toxic accumulation of bile in the bile ducts leads to cholangiocyte activation and ductular reaction proliferation, and is positive for Sirius Red staining and Masson's trichrome staining.

The tissue staining of the cholestatic liver disease animal models was measured through H&E staining (basic tissue staining), Sirius Red staining (collagen staining), and Masson's trichrome staining (collagen, cytoplasm, muscle fibers, etc.), and the tissue staining was measured by a skilled researcher.

After the mice were fed a diet containing 0.1% DDC for 14 days, tissue staining was performed for inflammation, fibrosis, and adhesion molecules around the portal vein, and the results are shown in FIG. 1.

To investigate the preventive effect of β-Lapachone (BL) on cholestatic liver disease, the mice were fed a diet with 0 (DDC-vehicle), 40 mg/kg (DDC-BL40) and 80 mg/kg (DDC-BL80) 3 days before DDC treatment (total 17 days) and, after 3 days, were fed a diet with DDC (total 14 days). After 14 days of DDC treatment, the mice were sacrificed and the liver was harvested including the portal vein (PV) and bile ducts of the mice, and the surrounding lesions were confirmed by H&E, and are shown in FIG. 1.

As shown in FIG. 1, the DDC treatment group (DDC-vehicle) as a control group showed increased lesions (indicated by arrows) in the portal vein (PV) and bile ducts of the mice compared with the normal group (standard diet, SD). It was also identified that the DDC-induced cholestatic liver disease mice (DDC-BL40 and DDC-BL80) treated with β-lapachone (BL) showed significant lesion reductions (indicated by arrows) around the portal vein (PV) and bile ducts compared with the control group (DDC-vehicle) treated with a vehicle. It was also identified that the lesion reduction was significant in the group treated with 80 mg/kg (BL80) β-lapachone (BL) compared with the group treated with 40 mg/kg (BL40), indicating that β-lapachone (BL) reduced the lesions of the DDC-treated portal vein and bile ducts depending on the concentration thereof.

These results indicate that the β-lapachone treatment has a preventive effect, such as a reduction in lesions of the portal vein and bile ducts in the cholestatic liver disease occurrence environment.

2.2. Effect of β-Lapachone on Collagen Amount in Cholestatic Liver Disease Mouse Animal Models The liver harvested in Example 2.1 was investigated for tissues or connective tissues around cells through Sirius Red and Masson's trichrome staining, which are shown in FIG. 2A.

Figure 2:
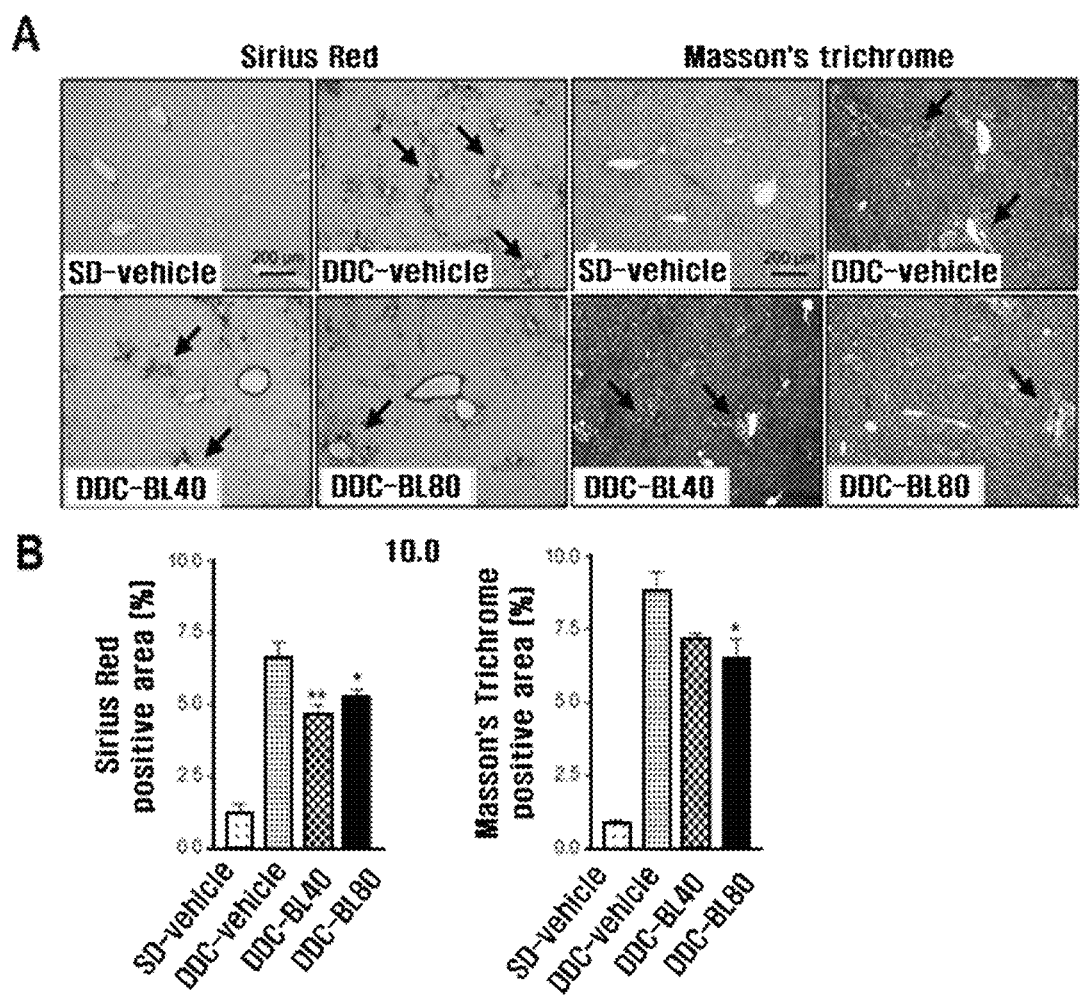
FIG. 2 shows effects of β-lapachone (BL) on the collagen tissue surrounding the portal vein in DDC-induced cholestatic liver disease animal models (Panel A: images of the tissue surrounding the portal vein stained with Sirius Red and Masson's trichrome, Panel B: Graphs of quantification of images of the tissue stained with Sirius Red and Masson's trichrome).

As shown in FIG. 2A, the Sirius Red and Masson's trichrome staining results confirmed that the formation of the connective tissues was increased by DDC and the β-lapachone treatment inhibited such fibrosis progression. FIG. 2B is a quantification of stained portions of FIG. 2A in digital images.

It can be seen from the results that the β-lapachone treatment had a preventive effect on fibrosis due to the increase in connective tissue in the cholestatic liver disease occurrence environment.

Statistical analysis was performed on the results obtained from independent experiments (means±SEM) throughout the entire examples by two-tailed Student's t-test. The differences were considered significant when $p<0.05$. As for survival comparison experiments, the results were plotted and analyzed according to Kaplan-Meier survival analysis or product-limit method, with a log-rank (Mantel-Cox) test (Prism, version 5.0, GraphPad Software).

2.3. Identification of Effect of β-Lapachone on (mRNA) Transcriptional Levels of Fibrosis-Associated Genes in Cholestatic Liver Disease Mouse Animal Models In the cholestatic liver disease mouse models, the bile ducts were damaged and fibrosis was induced, by DDC, and accordingly, the transcriptional levels of collagen type I alpha 1 (Col1α1), collagen type IV alpha 1 (Col4α1), alpha-smooth muscle actin (α-SMA), fibronectin, transforming growth factor beta 1 (TGF-β1), collagen type I alpha 2 (Col1α2), and transforming growth factor beta 2 (TGF-β2), which are important factors in the development of fibrosis, were confirmed to be increased.

The expression of the factors in the liver tissue obtained from the cholestatic liver disease mouse animal models of Example 2.1 was performed by a real-time polymerase chain reaction was performed according to the following procedure. Total RNA from liver samples was extracted using Tri-RNA Reagent (Favrogen BIOTECH CORP, Nong-Ke Rd, Taiwan) according to the procedure presented by Favrogen, and was reverse transcribed into cDNA by using PrimeScript™ RT reagent Kit with gDNA Eraser (TAKARA Korea Biomedical Inc, Seoul, 08506, Korea). Quantitative PCR was performed using TB Green™ Premix Ex Taq™ II (Tli RNaseH Plus), ROX plus (TAKARA Korea Biomedical Inc, Seoul, 08506, Korea) and QuantStudio 5 Real-Time PCR Instrument (Thermo Fisher Scientific, Waltham, MA, USA). The primer sequences used are shown in Table 1 below.

TABLE 1

| Gene name | Primer Category | Sequence |
|---|---|---|
| Col1a1 | Forward | 5'-CCTGAGTCAGCAGATTGAGAACA-3' |
|  | Reverse | 5'-CCAGTACTCTCCGCTCTTCCA-3' |
| Col1a2 | Forward | 5'-TTCTGCAGGGTTCCAACGAT-3' |
|  | Reverse | 5'-TGTCTTGCCCCATTCATTTG-3' |
| Fibronectin | Forward | 5'-AGGCAGAAAACAGGTCTCGATT-3' |
|  | Reverse | 5'-CAGAATGCTCGGCGTGATG-3' |
| α-Sma | Forward | 5'-CACGGCATCATCACCAACTG-3' |
|  | Reverse | 5'-GGCCACACGAAGCTCGTTAT-3' |
| TGFβ1 | Forward | 5'-GCAGTGGCTGAACCAAGGA-3' |
|  | Reverse | 5'-AGAGCAGTGAGCGCTGAATC-3' |
| TGFβ2 | Forward | 5'-CAGCGCTACATCGATAGCAA-3' |
|  | Reverse | 5'-CCTCGAGCTCTTCGCTTTTA-3' |

Figure 3:
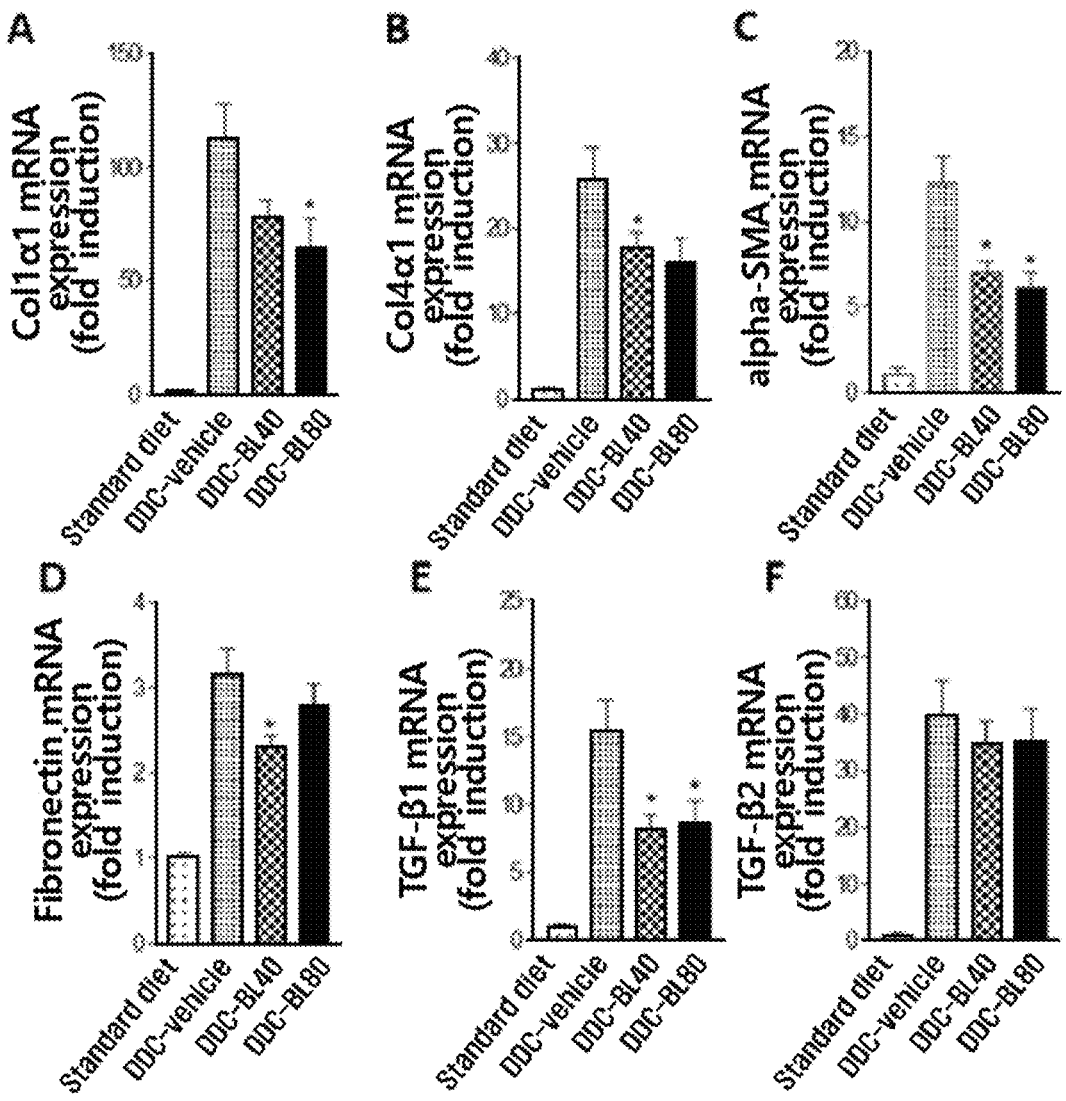
FIG. 3 presents graphs showing effects of β-lapachone (BL) on expression of fibrosis-related genes in DDC-induced cholestatic liver disease mice (n=6).

The DDC-induced cholestatic liver disease mice also treated with β-lapachone were investigated for the transcriptional levels of collagen type I alpha 1 (Col1α1), collagen type IV alpha 1 (Col4α1), alpha-smooth muscle actin (α-SMA), fibronectin, transforming growth factor beta 1 (TGF-β1), and transforming growth factor beta 2 (TGF-β2), which are fibrosis-related genes associated with the progress of cholestatic liver disease, and compared with the vehicle-treated mice as the control group in view of expression levels, and the results are shown in FIG. 3. As shown in FIGS. 3A to 3F, similar to the results of the reductions in portal vein lesions and fibrosis, the transcriptional levels of Col1α1, Col4α1, α-SMA, fibronectin, and TGF-β1 were significantly reduced in the DCC-induced cholestatic liver disease mice (DDC-BL40 and DDC-BL80) treated with β-lapachone (BL) compared with the DCC-induced cholestatic liver disease mice (DDC-vehicle) treated with a vehicle. These results in the DDC-induced cholestatic liver disease mice indicate that the reductions in portal vein lesions and fibrosis were made at the level of fibrosis-related gene expression, and pathological changes during the occurrence of cholestatic liver disease were inhibited by the pre-treatment with β-lapachone (BL).

Example 3: Identification of Effect of β-Lapachone in Cholestatic Liver Disease Mouse Animal Models To investigate the effect of β-lapachone (BL) on the occurrence of cholestatic liver disease, both 1% DDC and β-lapachone were administered to mice to characterize animal models.

3.1. Identification of Effect on Blood Indexes (ALT, AST, ALP, and Bilirubin)

After 8-week-old C57BL/6 male mice (Samtako, Korea) were divided into each group (=6), the mice were fed a diet with normal (vehicle), control (DDC), DDC-+β-lapachone 20 mg/kg, DDC+β-lapachone 40 mg/kg, DDC+β-lapachone 80 mg/kg, DDC+β-lapachone 100 mg/kg, and positive control DDC+ursodeoxycholic acid 100 mg/kg, and DDC+obeticholic acid 30 mg/kg (total 7 days). After 7 days of treatment, the mice were sacrificed and then the blood was collected from the heart. Thereafter, the levels of alanine aminotransferase (ALT), aspartate aminotransferase (AST), alkaline phosphatase (ALP), and bilirubin, which are blood indexes, were analyzed, and shown in FIG. 4.

Figure 4:
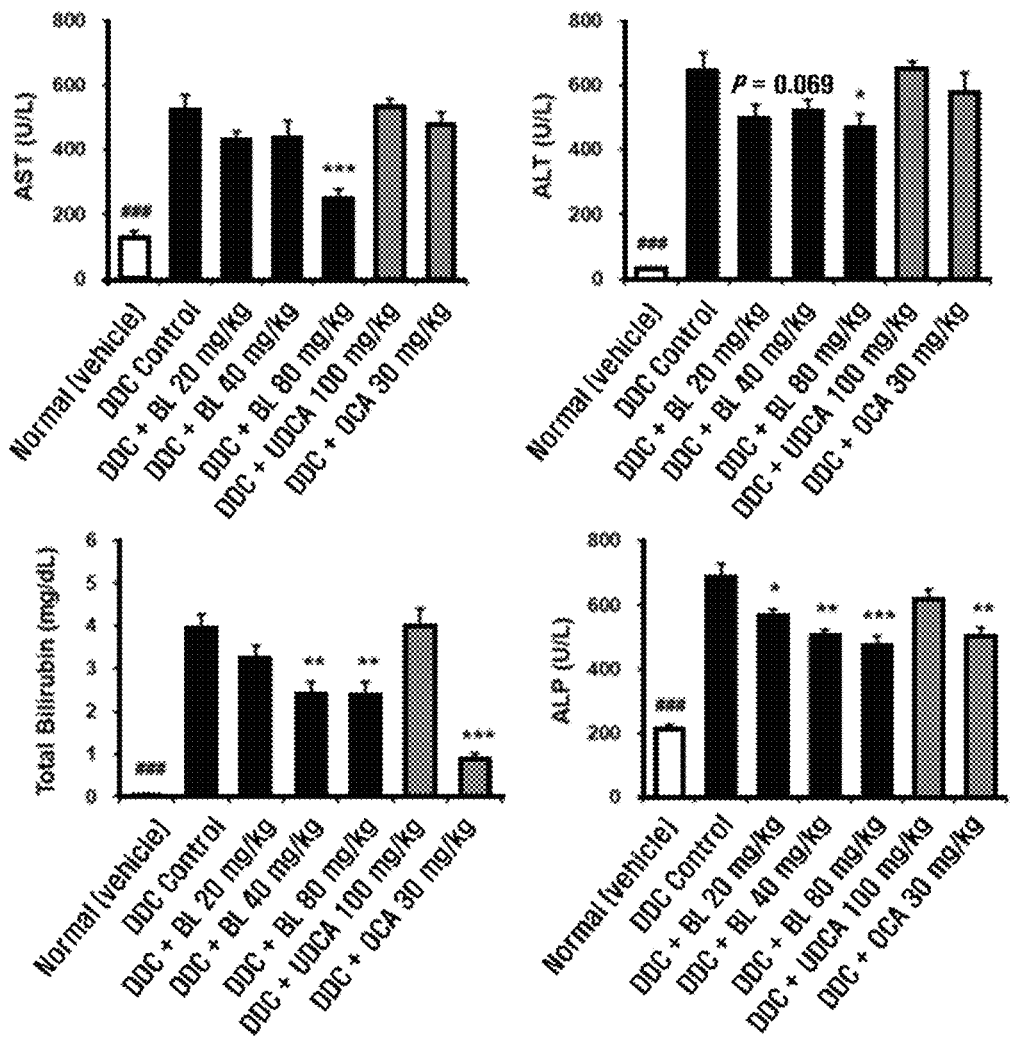
FIG. 4 presents graphs showing effects of β-lapachone (BL) on blood indexes (ALT, AST, ALP, and bilirubin) in DDC-induced cholestatic liver disease mice (n=6).

As shown in FIG. 4, the DDC treatment significantly increased the levels of ALT, AST, ALP, and bilirubin in the blood, and β-lapachone (BL) inhibited ALT, AST, ALP, and bilirubin, increased by the DDC treatment, depending on the concentration thereof, and showed excellent effects compared with ursodeoxycholic acid (UDCA) and obeticholic acid (OCA).

3.2. Identification of Effect on Transcriptional Levels of Fibrosis-Related Genes After the cholestatic liver disease mouse animal models in Example 3.1 were sacrificed and the liver tissue was harvested therefrom, the mRNA levels of fibrosis-related genes were measured by a method similar to the method in Example 2.3.

Figure 5:
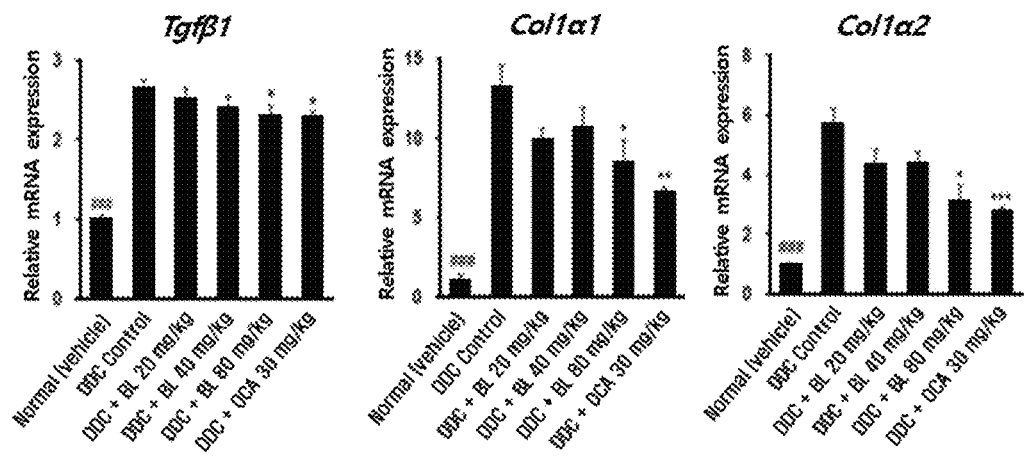
FIG. 5 presents graphs showing effects of β-lapachone (BL) on expression of fibrosis-related genes in DDC-induced cholestatic liver disease mice (n=6).

In the cholestatic liver disease mouse models, the bile ducts were damaged and fibrosis was induced, by DDC, and accordingly, the transcriptional levels of collagen type I alpha 1 (Col1α1), transforming growth factor beta 1 (TGF-β1), and collagen type I alpha 2 (Col1α2), which are important factors in the development of fibrosis, were investigated, and the results are shown in FIG. 5.

As shown in FIG. 5, DDC significantly increased the transcriptional levels of Col1α1, TGF-β1, and Col1α2, which are genes associated with fibrosis, and β-lapachone (BL) inhibited the transcriptional levels of Col1α1, TGF-β1, and Col1α2 depending on the concentration thereof.

3.3. Identification of Effect on Transcriptional Levels of Inflammation-Related Genes In the cholestatic liver disease, the inflammation in the portal vein and damage to the bile ducts in the liver occur chronically, resulting in cholestasis and liver fibrosis. The mRNA levels of inflammatory cytokine genes in the liver tissue of the cholestatic liver disease mouse animal models obtained by the same method as in Example 3.1 were measured, and shown in FIG. 6. The primer sequences used for gene expression analysis are shown in Table 2 below.

TABLE 2

| Gene name | Primer Category | Sequence |
|---|---|---|
| TNFα | Forward | 5'-CTGAGGTCAATCTGCCCAAGTAC-3' |
|  | Reverse | 5'-CTTCACAGAGCAATGACTCCAAAG-3' |
| IL-1β | Forward | 5'-GAAAGCTCTCCACCTCAATGG-3' |
|  | Reverse | 5'-AGGCCACAGGTATTTTGTCGT-3' |

Figure 6:
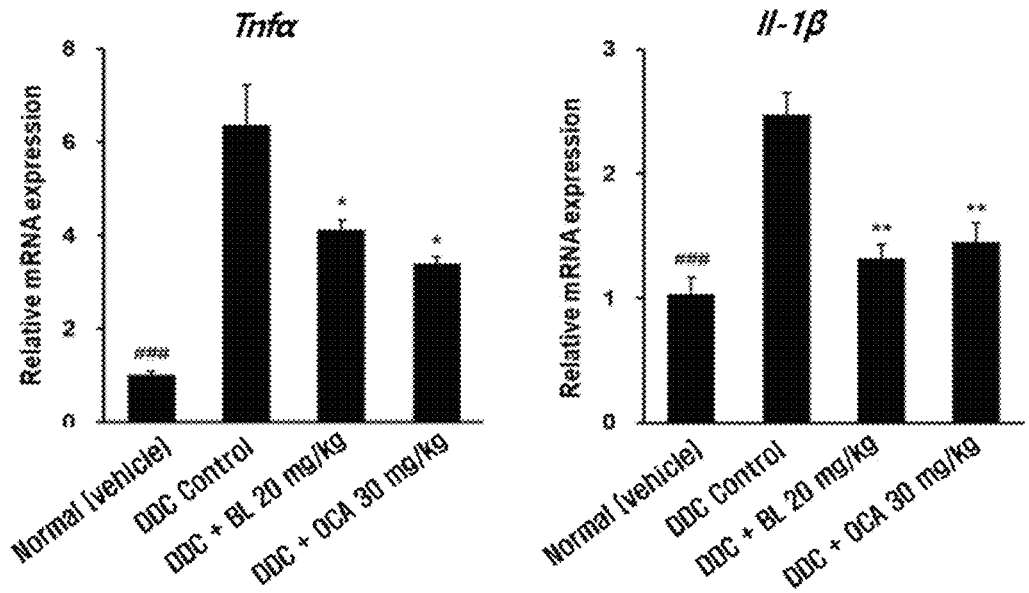
FIG. 6 presents graphs showing effects of β-lapachone (BL) on expression of inflammation-related genes in DDC-induced cholestatic liver disease mice (n=6).

As shown in FIG. 6, DDC significantly increased the transcriptional levels of TNFα and IL-1β, which are inflammation-related genes, and β-lapachone (BL) inhibited the transcriptional levels of TNFα and IL-1β.

Example 4: Identification of Treatment Effect of β-Lapachone in Cholestatic Liver Disease-Induced Mouse Animal Models The treatment effect of β-lapachone in cholestatic liver disease-induced mouse animals were investigated. After 8-week-old C57BL/6 male mice (Samtako, Korea) were divided into each group (=6), each group excluding a control group was fed a diet containing 0.1% DDC for 3 days. Thereafter, the mice were fed a diet with DDC control (vehicle), DDC-+β-lapachone 20 mg/kg, DDC-+β-lapachone 40 mg/kg, DDC-+β-lapachone 80 mg/kg, and positive control DDC+obeticholic acid 30 mg/kg for 4 days (total 7 days). After 7 days of feeding, the mice were sacrificed and then the blood was collected from the heart. Thereafter, the levels of bilirubin and ALP, which are blood indexes, were analyzed, and shown in FIG. 7.

Figure 7:
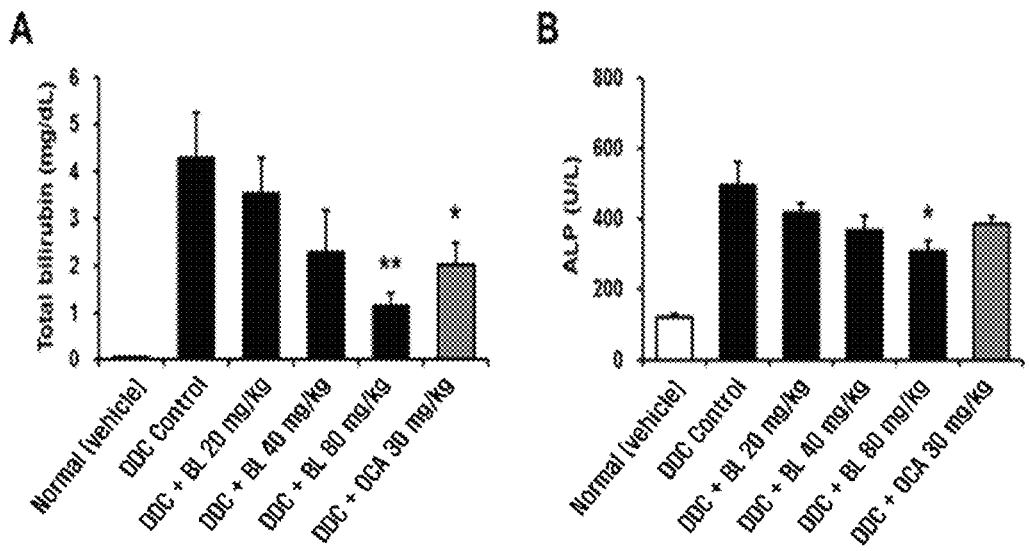
FIG. 7 presents graphs showing effects of β-lapachone (BL) on blood indexes (total bilirubin and ALP) in DDC-induced cholestatic liver disease animal models.

As shown in FIG. 7, the DDC treatment significantly increased the levels of bilirubin and ALP in the blood, and β-lapachone inhibited bilirubin and ALP, increased by the DDC treatment, depending on the concentration thereof. In addition, β-lapachone showed an excellent effect compared with ursodeoxycholic acid (UDCA) and obeticholic acid (OCA).

Example 5: Identification of Treatment Effect of β-Lapachone in Primary Biliary Cirrhosis (PBC)-Induced Mouse Animal Models Of cholestatic liver diseases, primary biliary cirrhosis (PBC) may be introduced to a similar state by using a viral RNA mimic and the Toll-like receptor polyinosinic-polycytidylic acid (Poly I:C).

After 8-week-old C57BL/6 male mice (Samtako, Korea) were divided into each group (=6), each experimental group excluding a normal group was intraperitoneally administered 5 mg/kg Poly I:C twice a week for 8 weeks. Thereafter, the mice were fed a diet with control (vehicle), β-lapachone 40 mg/kg, β-lapachone 80 mg/kg, and positive control ursodeoxycholic acid 100 mg/kg and obeticholic acid 30 mg/kg for 8 weeks. On the 16th week of treatment, the experiment was ended, and the mice were sacrificed and then the blood was collected from the heart. Thereafter, the levels of the blood indexes AST, ALT, and ALP were analyzed, and shown in FIG. 8.

Figure 8:
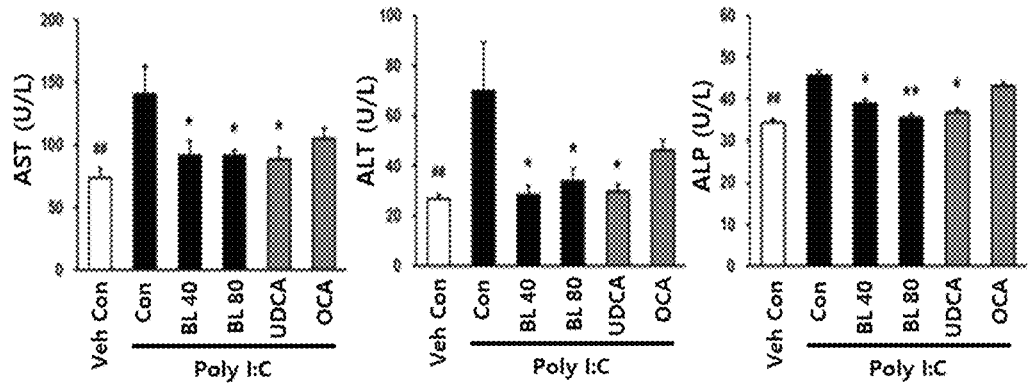
FIG. 8 presents graphs showing effects of β-lapachone (BL) on the blood indexes AST, ALT, and ALP in Poly I:C-induced cholestatic liver disease animal models.

As shown in FIG. 8, the levels of AST, ALT, and ALP in the blood were increased by Poly I:C, and β-lapachone (BL) inhibited AST, ALT, and ALP, increased by Poly I:C. UDCA among the controls inhibited AST, ALT, and ALP increased by DDC, but β-lapachone (BL) showed an excellent effect compared with the comparative substances ursodeoxycholic acid (UDCA) and obeticholic acid (OCA).

Example 6: Identification of Treatment Effect of β-Lapachone in Inflammatory Bowel Disease-Induced Mouse Animal Models Approximately 80% of cholestatic liver disease patients suffer from inflammatory bowel disease (IBD), and thus the present inventors identified the effect of β-lapachone (BL) in inflammatory bowel disease mouse animal models.

6.1. Effects on Survival Rate, Body Weight, Colitis Score

Dextran sodium sulfate (DSS)-induced acute colitis mouse models were constructed using 8-week-old C57BL/6 female mice (Samtako, Korea).

After 8-week-old C57BL/6 female mice (Samtako, Korea) were divided into each group (=10), each experimental group was fed a standard rodent diet supplemented with 3% (w/w) DSS in drinking water for the first 5 days to induce acute colitis and orally administered control (vehicle), β-lapachone 40 mg/kg, and β-lapachone 80 mg/kg for 14 days.

Figure 9:
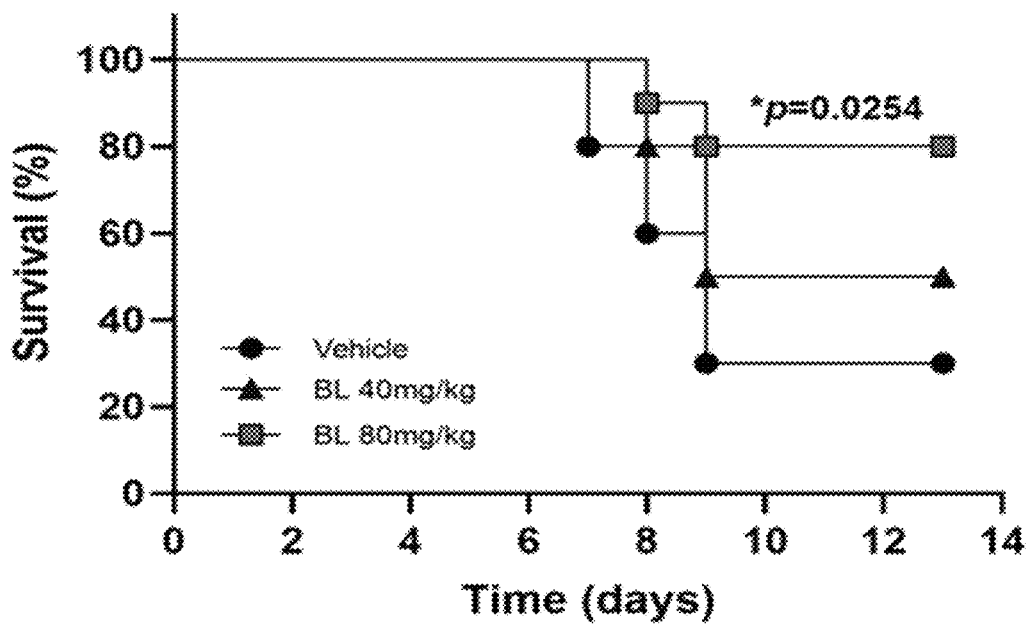
FIG. 9 presents a graph showing effects of β-lapachone (BL) on the survival rate of inflammatory bowel disease mice in DSS-induced inflammatory bowel disease mice.

All animal-related procedures were discussed and approved by the Institutional Animal Care and Use Committee of the Hanyang University. The survival rate over time is shown in FIG. 9, and the change rate in body weight of mice in each experimental group was measured and shown in FIG. 10A. The fecal occult bleeding per rectum, total bleeding loss, and fecal concentration were measured daily. As for the colitis score of each experimental group, the body weight reduction, bloody feces, firmness of feces, and the like were measured by two skilled researchers unaware of the treatment group, and convert to score as shown in Table 3, and the sum thereof was calculated and shown in FIG. 10B.

TABLE 3

| Score | Body weight reduction | Feces condition | Blood feces |
|---|---|---|---|
| 0 | No body weight reduction | Well-formed granular form | No bleeding |
| 1 | 1-5% reduction | | |
| 2 | 5-10% reduction | Paste form that is not attached to the anus or semi-formed granular form | Partial bleeding |
| 3 | 10-20% reduction | | |
| 4 | 20% or more reduction | Liquid form that is attached to the anus | Overall bleeding |

Figure 10:
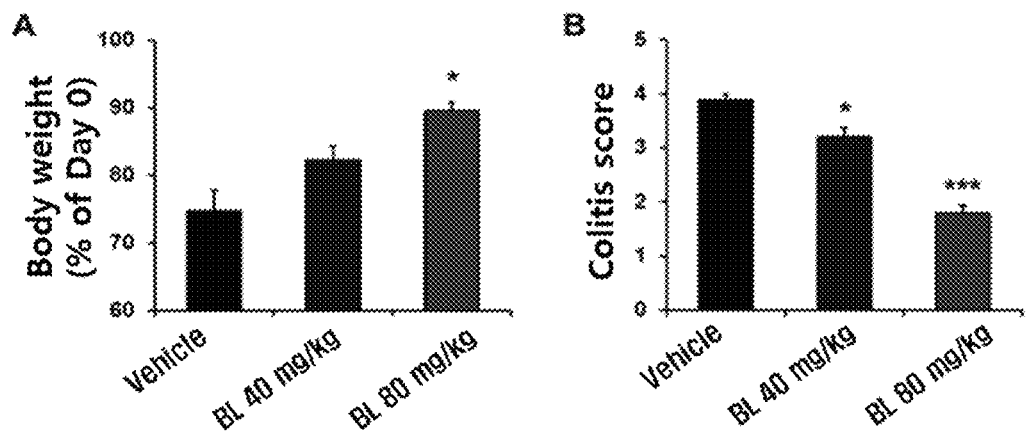
FIG. 10 presents graphs showing the effects of β-lapachone on the body weight change (A) and the colitis score (B) in DSS-induced inflammatory bowel disease mice (n=10).

As shown in FIG. 9, 70% died in the DSS-induced IBD mice, and 50% died in the β-lapachone 40 mg/kg experimental group, and only 20% died in the β-lapachone 80 mg/kg experimental group on the 14th day of the experiment. As shown in FIG. 10A, the body weight of the DSS-induced IBD mice was reduced, and reduced to 75% relative to baseline on Day 8 of the initiation of the experiment. In the groups treated with β-lapachone (BL), the body weight reduction by DSS was inhibited, and especially, the β-lapachone 80 mg/kg experimental group was recovered up to 90% of the initial body weight. As shown in FIG. 10B, the colitis score of the DSS-induced IBD mice was reduced depending on the treatment concentration of β-lapachone (BL).

6.2. Effects on Colon Length Recovery and Inflammation Inhibition

By the same method as in Example 6.1, experimental groups were divided into a DSS untreated group (Control), a DSS treated group, and a DSS-+β-lapachone 80 mg/kg treated group, respectively, and treated. After the end of the experiment, the mice were sacrificed to remove the colon, and the accurate colon length was measured using a Vernier caliper, and is shown FIGS. 11A and 11B. In addition, the mRNA levels of genes of interleukin-1beta (IL-1β), interleukin-6 (IL-6), interleukin-18 (IL-18), interferon-γ (INF-γ), tumor necrosis factor-α (TNF-α), tumor necrosis factor-β (TNF-β), and monocyte chemoattractant protein-1 (MCP-1), which were inflammatory cytokine factors in the colon tissue, were analyzed by a real-time polymerase chain reaction through a conventional experiment procedure, and are shown in FIG. 12.

Figure 11:
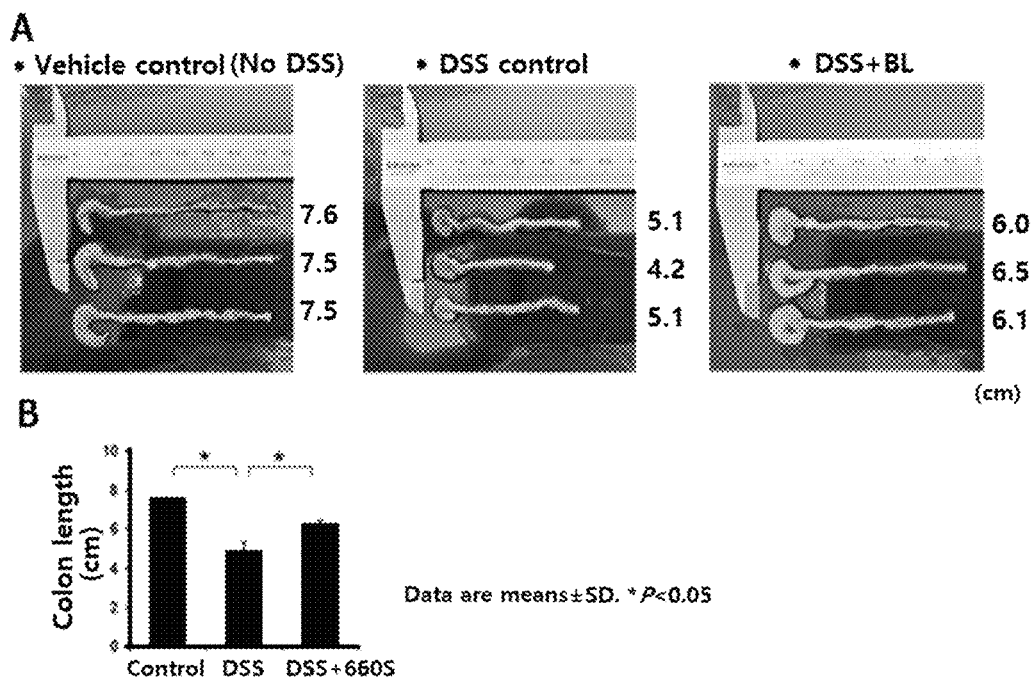
FIG. 11 presents colon length comparison images (A) and a graph showing same (B) in DSS-induced inflammatory bowel disease mice.
Figure 12:
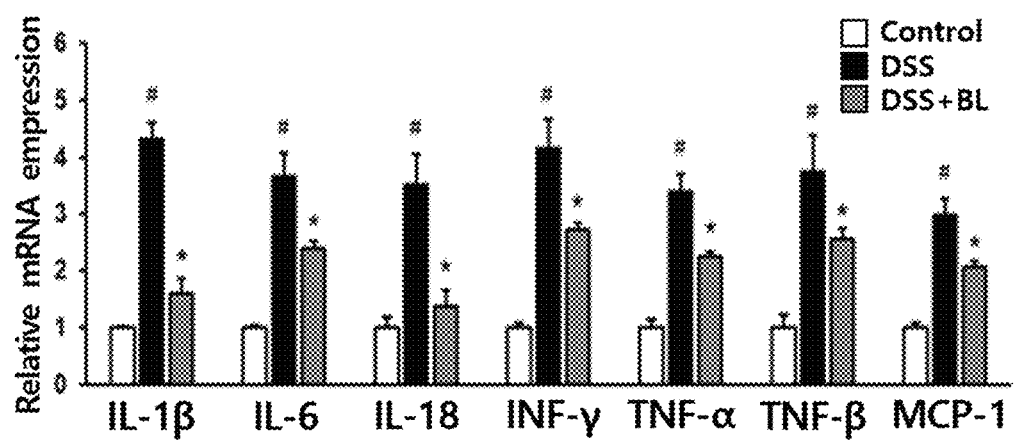
FIG. 12 presents a graph showing effects of β-lapachone (BL) on inflammatory cytokines of the colon tissue in DSS-induced inflammatory bowel disease mice.

As shown in FIGS. 11A and 11B, the colon length of the mice was significantly shortened by DSS, and was recovered by the β-lapachone (BL) treatment.

The inhibition of inflammation may include an inhibition of inflammatory cytokines and/or an inhibition of cytokine gene expression. In this regard, as shown in FIG. 12, the mRNA levels of IL-1β, IL-6, IL-18, INF-γ, TNF-α, TNF-β, and MCP-1, which are inflammatory factors in the colon tissues of mice, were significantly increased, and each of the inflammatory cytokines, increased by DSS, was significantly reduced by the β-lapachone treatment.

Example 7: Anti-Fibrotic Effect of β-Lapachone at Cell Level 7.1. Effect of β-Lapachone on Fibronectin and α-SMA Activity in LX-2 Hepatic Stellate Cell Line Models Considering that inflammation and fibrosis of bile ducts cause cirrhosis in cholestatic liver disease, experiments were performed on the LX-2 hepatic stellate cell line model by using the method of Takaaki Higashi et al. (2017). The LX-2 cell line was subcultured in DMEM containing 10% FBS, 2 mM glutamine, 100 U penicillin, and 0.1 mg/ml streptomycin. The LX-2 cell line was added into a 6-well plate at a density of $16 \times 10^4$ cells/well, and cultured in DMEM containing 1 ng/ml TGF-β1, 1 ng/ml TGF-β1+0.5 μM β-lapachone or 1 ng/ml TGF-β1+1 μM β-lapachone for 24 hours. Thereafter, the protein expression levels of the fibrosis-related genes fibronectin and α-SMA of the obtained cells were measured by protein immunoblotting according to a conventional method known in the art.

Figure 13:
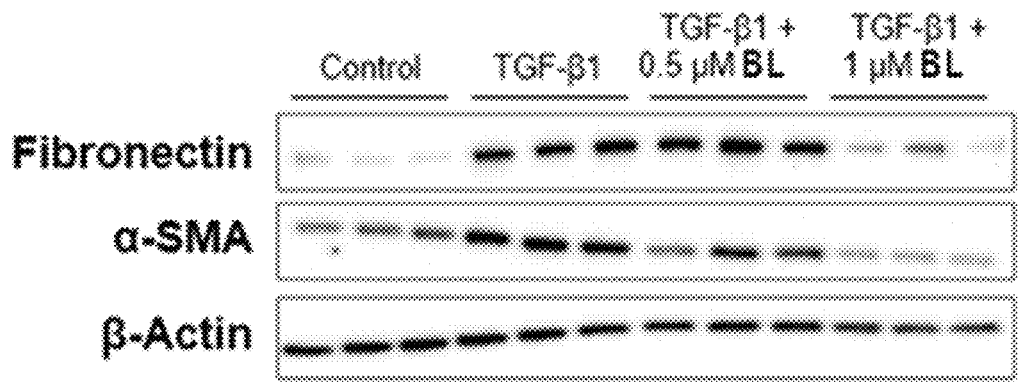
FIG. 13 presents a graph showing effects of β-lapachone (BL) on fibrosis-related mRNA expression in LX-2 hepatic stellate cell models.

As shown in FIG. 13, when the control group LX-2 cell line was treated with TGF-β1, the protein expression levels of fibronectin and α-smooth muscle actin (α-SMA) associated with fibrosis were increased compared with the control group, but in the case of the administration of β-lapachone, the levels of fibronectin and α-SMA increased by TGF-β1 were reduced depending on the concentration of β-lapachone.

7.2. Effect of β-Lapachone on Inflammatory Cytokine Protein Expression in Macrophage Line Raw264.7 Cell Model The macrophage line Raw264.7 (ATCC TIB-71, Manassas, VA, USA) was subcultured in DMEM supplemented with 10% FBS and 1% penicillin/streptomycin.

For inflammation induction, RAW264.7 cells were suspended in DMEM containing 2% FBS, inoculated in a 12-well plate to a cell number of $4 \times 10^5$/ml, and incubated in 5% $CO_2$ incubator at 37° C. for 24 hours. With replacement with fresh media, the cells were treated with appropriate concentrations of a corresponding substance, LPS (100 ng/ml), and 0.2, 0.5, 1, and 2 μM β-lapachone, cultured for 24 hours, treated with ATP (2.5 mM), and then cultured for additional 30 minutes, and the supernatant was collected. The release of cytokines (IL-1β and TNF-α) of RaW264.7 macrophages was quantified using each cell-free supernatant-ELISA set (Invitrogen, Billerica, MA, USA) by Invitrogen according to the manufacture's instruction, and is shown in FIG. 14.

Figure 14:
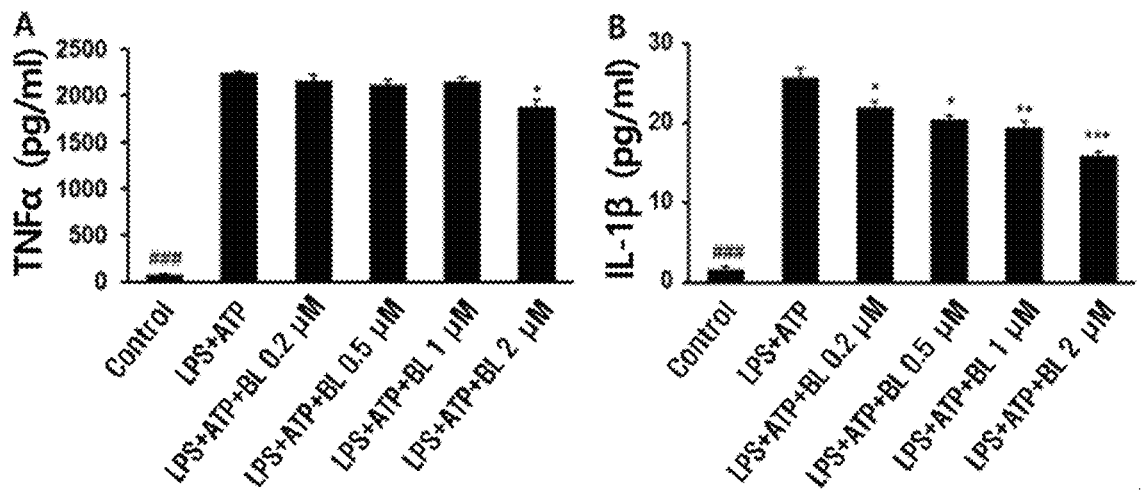
FIG. 14 presents graphs showing effects of β-lapachone on expression of the inflammatory cytokine proteins IL-1β and TNF-α in the macrophage line Raw264.7 cell model.

As shown in FIG. 14, when the Raw264.7 cell line was treated with LPS and ATP, the expression of inflammation-related proteins, IL-1β and TNF-α, was increased compared with the control group, but in cases of the administration of β-lapachone (BL), the expression levels of IL-1β and TNF-α protein, increased by LPS and ATP, was reduced depending on the concentration of β-lapachone.

7.3. Effect of β-Lapachone on Secretion of Inflammatory Cytokines 1L-1β and IL-18 in Peripheral Blood Mononuclear Cells (PMBCs)

Figure 15:
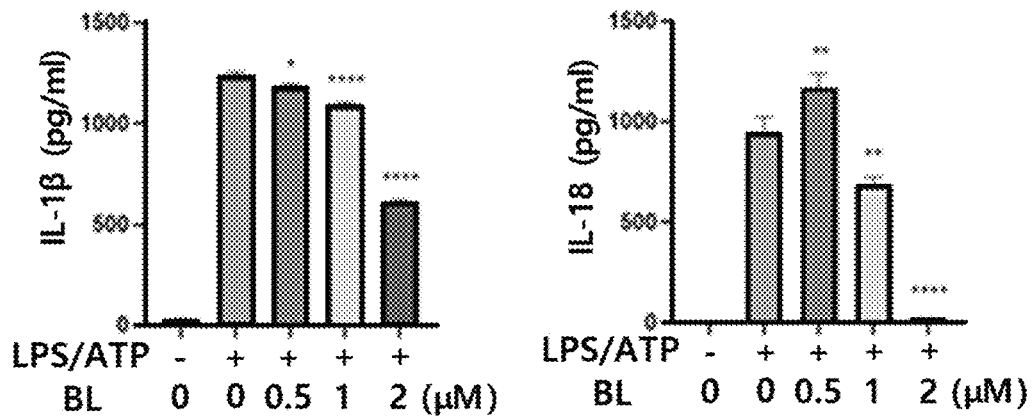
FIG. 15 presents graphs showing effects of β-lapachone (BL) on expression of the inflammatory cytokines IL-1β and IL-18 proteins in peripheral blood mononuclear cells (PMBCs).

Considering that inflammatory cytokines mediate the pathogenic mechanism of cholestatic liver disease, the peripheral blood mononuclear cell model was used by a modified method of Boyum et al. (1968). Peripheral blood mononuclear cells isolated from healthy 8-week-old C57BL/6 male mice (Samtako, Korea) were maintained by primary culture in RPMI-1640 medium containing 10% FBS, 2 mM glutamine, 100 U penicillin, and 0.1 mg/ml streptomycin. Stable peripheral blood mononuclear cells (PBMCs) were treated with LPS at 200 ng/mL and ATP and β-lapachone at 0, 0.5, 1, 2 μM in the medium and, after 4 hours, the expression levels of IL-1β and IL-18 were investigated, and the results are shown in FIG. 15.

As shown in 15, when the Peripheral blood mononuclear cells were treated with LPS and ATP, the expression levels of inflammation-related proteins, IL-1β and IL-18, were increased compared with the control group, but in cases of the administration of β-lapachone (BL), the expression levels of IL-1β and IL-18, increased by LPS and ATP, were reduced depending on the concentration of β-lapachone (BL).

The invention claimed is:

1. A method for prevention of treatment of cholestatic liver disease, comprising administering to a mammal in need thereof a therapeutically effective amount of a pharmaceutical composition containing β-lapachone or a pharmaceutically acceptable salt thereof as an active ingredient, wherein the cholestatic liver disease is at least one selected from the group consisting of primary biliary cirrhosis (PBC) and primary sclerosing cholangitis (PSC), and wherein the β-lapachone is administered at a dose of 20 mg/kg/day to 500 mg/kg/day.

2. The method of claim 1, wherein the composition inhibits fibrosis and inflammation of cholangiocytes.

3. The method of claim 1, wherein the composition improves the level of at least one blood index selected from the group consisting of AST, ALT, ALP, and bilirubin in the blood.

4. The method of claim 2, wherein the inhibiting of fibrosis comprises inhibiting at least one selected from fibrosis factors consisting of collagen type I alpha 1 (Colα1), collagen type IV alpha 1 (Col4α1), alpha-smooth muscle actin (α-SMA), fibronectin, transforming growth factor beta 1 (TGF-β1), collagen type I alpha 2 (Collα2), and transforming growth factor beta 2 (TGF-β2).

5. The method of claim of 2, wherein the inhibiting of inflammation comprises inhibiting at least one selected from inflammatory cytokine factors consisting of interleukin-1beta (IL-1β), interleukin-6 (IL-6), interleukin-18 (IL-18), interferon-γ (INF-γ), tumor necrosis factor-α (TNF-α), tumor necrosis factor-β (TNF-β), and monocyte chemoattractant protein-1 (MCP-1).

6. The method of claim 1, wherein the cholestatic liver disease is accompanied by inflammatory bowel disease.

7. The method of claim 6, wherein the inflammatory bowel disease is Crohn's disease or ulcerative colitis.

8. The method of claim 7, wherein the composition inhibits fibrosis and inflammatory cytokines in colon tissues.

* * * * *

SEQUENCE LISTING

```
Sequence total quantity: 16
SEQ ID NO: 1            moltype = DNA  length = 23
FEATURE                 Location/Qualifiers
misc_feature            1..23
                        note = Col1a1 F primer
source                  1..23
                        mol_type = other DNA
                        organism = synthetic construct
SEQUENCE: 1
cctgagtcag cagattgaga aca                                             23

SEQ ID NO: 2            moltype = DNA  length = 21
FEATURE                 Location/Qualifiers
misc_feature            1..21
                        note = Col1a1 R primer
source                  1..21
                        mol_type = other DNA
```

```
                         organism = synthetic construct
SEQUENCE: 2
ccagtactct ccgctcttcc a                                               21

SEQ ID NO: 3            moltype = DNA  length = 20
FEATURE                 Location/Qualifiers
misc_feature            1..20
                        note = Col1a2 F primer
source                  1..20
                        mol_type = other DNA
                        organism = synthetic construct
SEQUENCE: 3
ttctgcaggg ttccaacgat                                                 20

SEQ ID NO: 4            moltype = DNA  length = 20
FEATURE                 Location/Qualifiers
misc_feature            1..20
                        note = Col1a2 R primer
source                  1..20
                        mol_type = other DNA
                        organism = synthetic construct
SEQUENCE: 4
tgtcttgccc cattcatttg                                                 20

SEQ ID NO: 5            moltype = DNA  length = 22
FEATURE                 Location/Qualifiers
misc_feature            1..22
                        note = Fibronectin F primer
source                  1..22
                        mol_type = other DNA
                        organism = synthetic construct
SEQUENCE: 5
aggcagaaaa caggtctcga tt                                              22

SEQ ID NO: 6            moltype = DNA  length = 19
FEATURE                 Location/Qualifiers
misc_feature            1..19
                        note = Fibronectin R primer
source                  1..19
                        mol_type = other DNA
                        organism = synthetic construct
SEQUENCE: 6
cagaatgctc ggcgtgatg                                                  19

SEQ ID NO: 7            moltype = DNA  length = 20
FEATURE                 Location/Qualifiers
misc_feature            1..20
                        note = alpha-Sma F primer
source                  1..20
                        mol_type = other DNA
                        organism = synthetic construct
SEQUENCE: 7
cacggcatca tcaccaactg                                                 20

SEQ ID NO: 8            moltype = DNA  length = 20
FEATURE                 Location/Qualifiers
misc_feature            1..20
                        note = alpha-Sma R primer
source                  1..20
                        mol_type = other DNA
                        organism = synthetic construct
SEQUENCE: 8
ggccacacga agctcgttat                                                 20

SEQ ID NO: 9            moltype = DNA  length = 19
FEATURE                 Location/Qualifiers
misc_feature            1..19
                        note = TGFbeta1 F primer
source                  1..19
                        mol_type = other DNA
                        organism = synthetic construct
SEQUENCE: 9
gcagtggctg aaccaagga                                                  19

SEQ ID NO: 10           moltype = DNA  length = 20
FEATURE                 Location/Qualifiers
misc_feature            1..20
                        note = TGFbeta1 R primer
source                  1..20
```

-continued

```
                        mol_type = other DNA
                        organism = synthetic construct
SEQUENCE: 10
agagcagtga gcgctgaatc                                              20

SEQ ID NO: 11           moltype = DNA   length = 20
FEATURE                 Location/Qualifiers
misc_feature            1..20
                        note = TGFbeta2 F primer
source                  1..20
                        mol_type = other DNA
                        organism = synthetic construct
SEQUENCE: 11
cagcgctaca tcgatagcaa                                              20

SEQ ID NO: 12           moltype = DNA   length = 20
FEATURE                 Location/Qualifiers
misc_feature            1..20
                        note = TGFbeta2 R primer
source                  1..20
                        mol_type = other DNA
                        organism = synthetic construct
SEQUENCE: 12
cctcgagctc ttcgctttta                                              20

SEQ ID NO: 13           moltype = DNA   length = 23
FEATURE                 Location/Qualifiers
misc_feature            1..23
                        note = TNFalpha F primer
source                  1..23
                        mol_type = other DNA
                        organism = synthetic construct
SEQUENCE: 13
ctgaggtcaa tctgcccaag tac                                          23

SEQ ID NO: 14           moltype = DNA   length = 24
FEATURE                 Location/Qualifiers
misc_feature            1..24
                        note = TNFalpha R primer
source                  1..24
                        mol_type = other DNA
                        organism = synthetic construct
SEQUENCE: 14
cttcacagag caatgactcc aaag                                         24

SEQ ID NO: 15           moltype = DNA   length = 21
FEATURE                 Location/Qualifiers
misc_feature            1..21
                        note = IL-1beta F primer
source                  1..21
                        mol_type = other DNA
                        organism = synthetic construct
SEQUENCE: 15
gaaagctctc cacctcaatg g                                            21

SEQ ID NO: 16           moltype = DNA   length = 21
FEATURE                 Location/Qualifiers
misc_feature            1..21
                        note = IL-1beta R primer
source                  1..21
                        mol_type = other DNA
                        organism = synthetic construct
SEQUENCE: 16
aggccacagg tattttgtcg t                                            21
```